(12) United States Patent
Raskin

(10) Patent No.: US 6,776,755 B1
(45) Date of Patent: Aug. 17, 2004

(54) MALE PROSTHESIS AND STIMULATOR

(76) Inventor: Carol L. Raskin, 5850 SW. 9 Ter., Miami, FL (US) 33144

( * ) Notice: Subject to any disclaimer, the term of this patent is extended or adjusted under 35 U.S.C. 154(b) by 36 days.

(21) Appl. No.: 10/285,602

(22) Filed: Oct. 30, 2002

(51) Int. Cl.$^7$ .................................................. A61F 5/00
(52) U.S. Cl. ........................................ 600/39; 600/41
(58) Field of Search ..................... 600/39–41; 128/842, 128/844

(56) References Cited

U.S. PATENT DOCUMENTS

| | | | | |
|---|---|---|---|---|
| 4,893,616 A | * | 1/1990 | Immonen | 600/39 |
| 5,360,390 A | * | 11/1994 | Maanum | 600/39 |
| 5,522,787 A | * | 6/1996 | Evans | 600/39 |
| 5,622,186 A | * | 4/1997 | Schwartz | 128/842 |
| 6,015,379 A | * | 1/2000 | Sachse | 600/39 |
| 6,321,750 B1 | * | 11/2001 | Kelly | 128/844 |
| 6,651,667 B2 | * | 11/2003 | Osterberg | 128/844 |

* cited by examiner

*Primary Examiner*—John P. Lacyk

(57) ABSTRACT

Male prosthesis and stimulators enhance stimulation during intercourse. Male prostheses and stimulators add to the friction and stimulation of the penis and vaginal walls by increasing the penis's girth and by the use of a filling within the male prosthesis and stimulator. A hollow tube which is arctuate in shape encloses a filling. The hollow tube is sufficiently flexible so that it can be rolled along its circumference to facilitate application to and removal from the shaft of the penis. A ridge is attached to the outer surface of the tube to optionally receive the O-ring of a condom. The movement of the filling against the penis enhances the male participant's pleasure. The added penis girth, as well as the movement of the filling within the male prosthesis and stimulator, is appealing to the female participant. The male prosthesis and stimulator may be packaged in a sealed package or sealed container.

1 Claim, 4 Drawing Sheets

MALE PROSTHESIS AND STIMULATOR

BACKGROUND OF THE INVENTION

1. Field of the Invention

The present invention relates to a male prosthesis and stimulator for use in connection with sexual activities. The male prosthesis and stimulator has particular utility in connection with enhancing stimulation during intercourse.

2. Description of the Prior Art

Male prostheses and stimulators are desirable for enhancing stimulation during intercourse. A key objective of a sex act is for both of the involved parties to have a pleasurable experience. In the case of a male and female participant, pleasurable sensations are derived from stimulation of the penis and vaginal walls. Male prostheses and stimulators add to the friction and stimulation of the penis and vaginal walls by increasing the penis's girth and by the use of a filling within the male prosthesis and stimulator. The movement of the filling against the penis enhances the male participant's pleasure. The added penis girth, as well as the movement of the filling within the male prosthesis and stimulator, is appealing to the female participant.

The use of male erection facilitation sheaths and methods of use thereof is known in the prior art. For example, U.S. Pat. No. 5,622,186 to Schwartz discloses male erection facilitation sheaths and methods of use thereof. However, the Schwartz '186 patent does not have a ridge to receive the O-ring of a condom, and has further drawbacks of requiring user to adjust the contents of the internal chamber using a valve.

U.S. Pat. No. 4,224,933 to Reiling discloses a sexual stabilizer and stimulator that is worn on a penis for exciting both partners of a sex act. However, the Reiling '933 patent does not have an interior filling, and additionally does not have an arctuate shape.

Similarly, U.S. Pat. No. 5,623,946 to Hessel discloses a tubular protective device for protection against transfer of infectious matter during sexual intercourse that protects against the transfer of infectious matter during sexual intercourse. However, the Hessel '946 patent does not have opposing open ends, and cannot enclose a filling.

In addition, U.S. Pat. No. 5,806,523 to Shubin, Sr. discloses a prophylactic and prosthetic device that is a prophylactic device that may also be used as a male sex organ size enhancer. However, the Shubin, Sr. '523 patent does not have opposing open ends, and also does not have a filling.

Furthermore, U.S. Pat. No. Des. 431,865 to Norton et al. discloses a sex enhancer tool that fits around the base of a penis. However, the Norton et al. '865 patent does not have a tube, and further lacks opposing open ends differing in diameter.

Lastly, U.S. Pat. No. 6,015,379 to Sachse discloses an erection aid that stiffens the male member. However, the Sachse '379 patent does not have a filling, and has the additional deficiency of requiring the user to wrap the erection aid around their penis.

While the above-described devices fulfill their respective, particular objectives and requirements, the aforementioned patents do not describe a male prosthesis and stimulator that allows enhancing stimulation during intercourse. The Schwartz '186 patent make no provision for ridge to receive the O-ring of a condom. The Schwartz '186 patent requires the user to adjust the contents of the internal chamber using a valve. The Reiling '933 patent, the Hessel '946 patent, Shubin, Sr. '523 patent, and the Sachse '379 patent do not have an interior filling. The Reiling '933 patent lacks an arctuate shape. The Hessel '946 patent and the Shubin, Sr. '523 patent do not have opposing open ends. The Norton et al. '865 patent does not have a tube, and further lacks opposing open ends differing in diameter. The Sachse '379 patent requires the user to wrap the erection aid around their penis.

Therefore, a need exists for a new and improved male prosthesis and stimulator that can be used for enhancing stimulation during intercourse. In this regard, the present invention substantially fulfills this need. In this respect, the male prosthesis and stimulator according to the present invention substantially departs from the conventional concepts and designs of the prior art, and in doing so provides an apparatus primarily developed for the purpose of enhancing stimulation during intercourse.

SUMMARY OF THE INVENTION

In view of the foregoing disadvantages inherent in the known types of male erection facilitation sheaths and methods of use thereof now present in the prior art, the present invention provides an improved male prosthesis and stimulator, and overcomes the above-mentioned disadvantages and drawbacks of the prior art. As such, the general purpose of the present invention, which will be described subsequently in greater detail, is to provide a new and improved male prosthesis and stimulator which has all the advantages of the prior art mentioned heretofore and many novel features that result in a male prosthesis and stimulator which is not anticipated, rendered obvious, suggested, or even implied by the prior art, either alone or in any combination thereof.

To attain this, the present invention essentially comprises a hollow tube with opposing open ends and an interior with a ridge attached to its outer surface.

There has thus been outlined, rather broadly, the more important features of the invention in order that the detailed description thereof that follows may be better understood and in order that the present contribution to the art may be better appreciated.

The invention may also include a filling enclosed by the tube's interior. The tube may be flexible and have opposing open ends that differ in diameter. The outer surface of the tube may be arctuate in shape. There may be an outer wall and an inner wall that are connected by their opposing ends to enclose a filling. The outer wall and inner wall may be washable. The outer wall and inner wall may be cylindrical or arctuate in shape. The outer wall and inner wall may be sufficiently flexible so that they can be rolled along their circumference to facilitate application and removal of the invention. The outer surface of the outer wall may have an appearance that simulates the color, physical properties, and tactile feel of human flesh, and, when wet with water-soluble fluids, has relatively low friction similar to the human skin that it replicates. The outer surface of the outer wall may be adapted to receive the O-ring of a condom, and the adaptation may comprise a ridge attached to the outer surface of the outer wall. The inner surface of the inner wall may be sufficiently tacky in texture to removably stick to the skin of the male user. The filling may be made of gel, saline solution, and/or beads. The tube and ridge may be made of silicone, polyurethane, polypropylene film, polyethylene terephthalate film, ethylene/vinyl acetate copolymer films, ultra-high molecular weight polyethylene, polyester block amides, polyester elastomers, vinyl materials, or latexes.

The invention may also be packaged in a sealed package or sealed container. There are, of course, additional features of the invention that will be described hereinafter and which will form the subject matter of the claims attached.

Numerous objects, features, and advantages of the present invention will be readily apparent to those of ordinary skill in the art upon a reading of the following detailed description of presently current, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved male prosthesis and stimulator that has all of the advantages of the prior art male erection facilitation sheaths and methods of use thereof and none of the disadvantages.

It is another object of the present invention to provide a new and improved male prosthesis and stimulator that may be easily and efficiently manufactured and marketed.

An even further object of the present invention is to provide a new and improved male prosthesis and stimulator that has a low cost of manufacture with regard to both materials and labor, and which accordingly is then susceptible of low prices of sale to the consuming public, thereby making such male prosthesis and stimulator economically available to the buying public.

Still another object of the present invention is to provide a new male prosthesis and stimulator that provides in the apparatuses and methods of the prior art some of the advantages thereof, while simultaneously overcoming some of the disadvantages normally associated therewith.

Even still another object of the present invention is to provide a male prosthesis and stimulator for enhancing stimulation during intercourse. This allows the male user to easily apply and remove the male prosthesis and stimulator.

Still yet another object of the present invention is to provide a male prosthesis and stimulator for enhancing stimulation during intercourse. This makes it possible to clean the male prosthesis and stimulator.

An additional object of the present invention is to provide a male prosthesis and stimulator for enhancing stimulation during intercourse. This stimulates both the male and the female partner, thereby increasing their pleasure.

A further object of the present invention is to provide a male prosthesis and stimulator for enhancing stimulation during intercourse. This permits effective use of a condom with the male prosthesis and stimulator.

Lastly, it is an object of the present invention to provide a new and improved male prosthesis and stimulator for enhancing stimulation during intercourse.

These together with other objects of the invention, along with the various features of novelty that characterize the invention, are pointed out with particularity in the claims annexed to and forming a part of this disclosure. For a better understanding of the invention, its operating advantages, and the specific objects attained by its uses, reference should be had to the accompanying drawings and descriptive matter in which there is illustrated current embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various figures.

DESCRIPTION OF THE CURRENT EMBODIMENT

Figure 1:
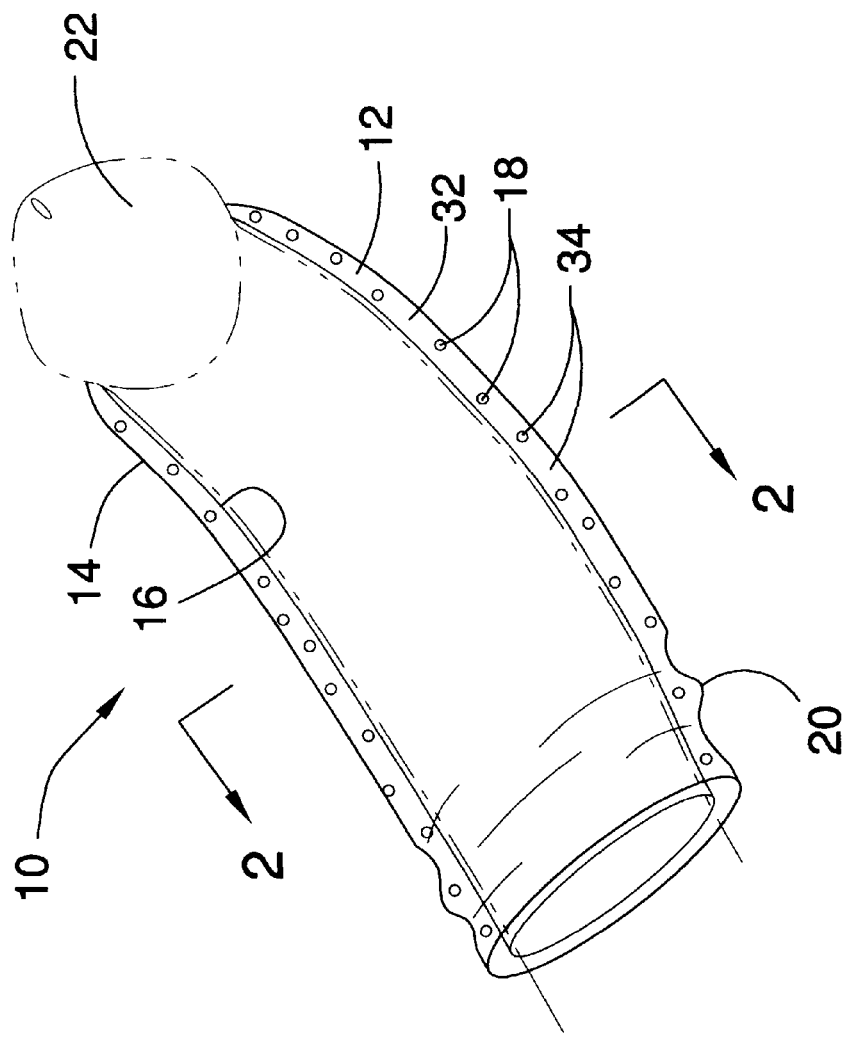
FIG. 1 is a top perspective view of the current embodiment of the male prosthesis and stimulator constructed in accordance with the principles of the present invention.

Referring now to the drawings, and particularly to FIGS. 1–4, a current embodiment of the male prosthesis and stimulator of the present invention is shown and generally designated by the reference numeral 10.

In FIG. 1, a new and improved male prosthesis and stimulator 10 of the present invention for enhancing stimulation during intercourse is illustrated and will be described. More particularly, the male prosthesis and stimulator 10 is shown in use with a tube 12 enclosing the shaft of penis 22. Tube 12 has an outer wall 14 and an inner wall 16 enclosing an interior 32. In the current embodiment, beads 18 are the filling 34 present in the interior 32. A ridge 20 is attached to the outer surface of outer wall 14. Tube 12 is arctuate in shape and has opposing open ends that differ in diameter. The shape of tube 12 exposes the glans of penis 22 to permit direct stimulation and fits snugly about the shaft of penis 22. The movement of beads 18 promotes pleasurable sensations in penis 22. Ridge 20 and tube 12 are made of silicone in the current embodiment. Note that the broken lines illustrating penis 22 are for illustrative purposes only and are not part of the current invention.

Figure 2:
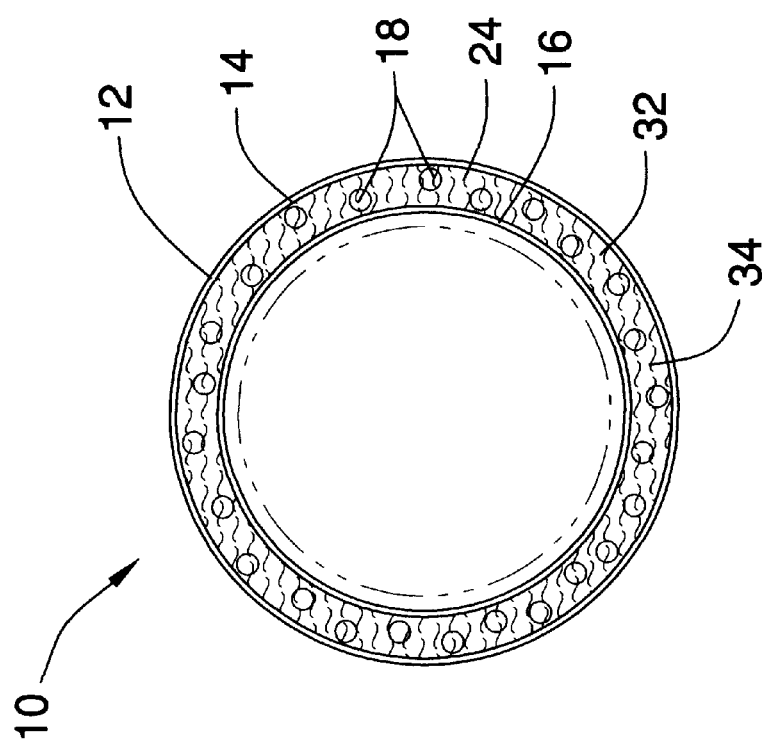
FIG. 2 is a side sectional view of the male prosthesis and stimulator of the present invention.

Moving on to FIG. 2, a new and improved male prosthesis and stimulator 10 of the present invention for enhancing stimulation during intercourse is illustrated and will be described. More particularly, the male prosthesis and stimulator 10 has a tube 12 consisting of an interior 32 between outer wall 14 and inner wall 16. Filling 34, in this case gel 24 and beads 18, is enclosed by interior 32. The movement of gel 24 and beads 18 promotes pleasurable sensations in penis 22 (not shown).

Figure 3:
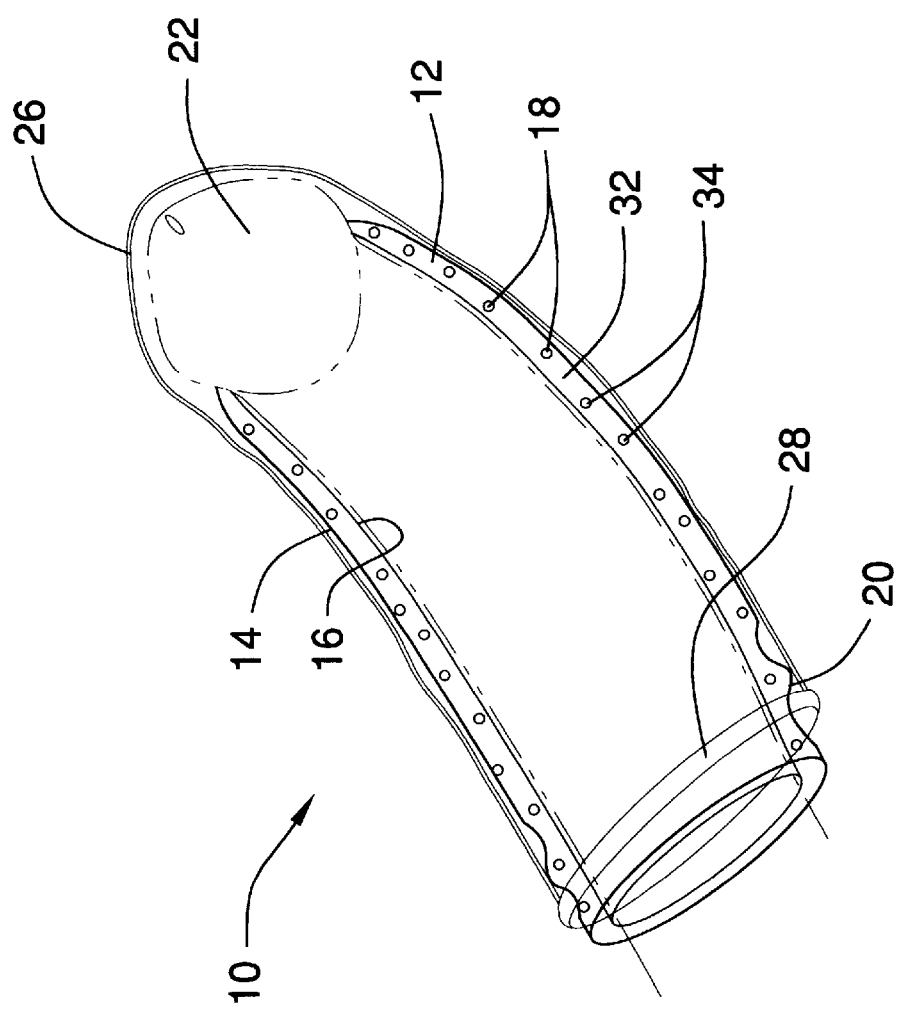
FIG. 3 is a top perspective view of the male prosthesis and stimulator of the present invention.

Continuing with FIG. 3, a new and improved male prosthesis and stimulator 10 of the present invention for enhancing stimulation during intercourse is illustrated and will be described. More particularly, the male prosthesis and stimulator 10 is shown in use with a condom 26 covering penis 22 and the outer wall 14 of tube 12. The O-ring 28 of condom 26 engages with ridge 20 to secure condom 26 over penis 22. Friction between inner wall 16 and the shaft of penis 22 keeps the male prosthesis and stimulator 10 in place. The movement of filling 34, in this case beads 18, within interior 32 stimulates penis 22 in a pleasurable fashion. Note that the condom 26 and the broken lines illustrating penis 22 are for illustrative purposes only and are not part of the current invention.

Figure 4:
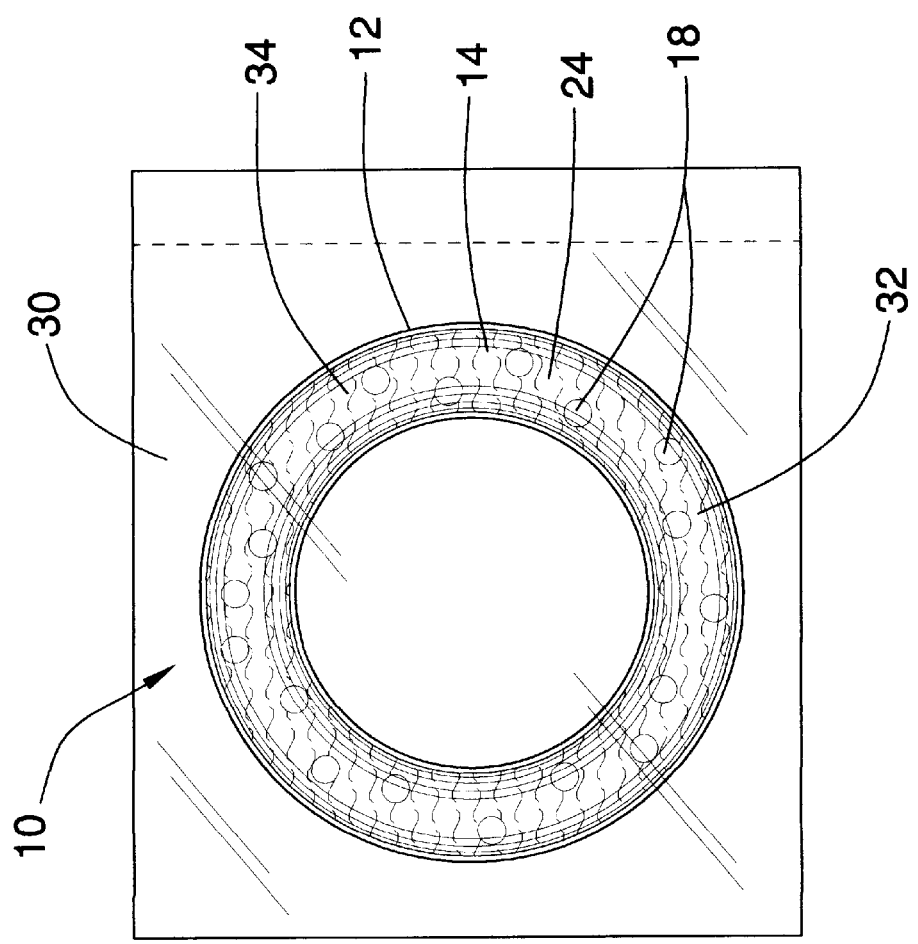
FIG. 4 is a top side view of the male prosthesis and stimulator of the present invention.

In FIG. 4, a new and improved male prosthesis and stimulator 10 of the present invention for enhancing stimulation during intercourse is illustrated and will be described. More particularly, the male prosthesis and stimulator 10 is packaged inside of container 30. Tube 12 is rolled along its circumference to facilitate storage and application of the male prosthesis and stimulator 10. In this position, inner wall 14 is the exterior surface. Filling 34, consisting of gel 24 and beads 18, is visible within interior 32.

In use, it can now be understood that the user opens container 30 and removes the male prosthesis and stimulator 10. The male prosthesis and stimulator 10 is rolled along its circumference to facilitate storage and application of the male prosthesis and stimulator 10. The user applies the male prosthesis and stimulator 10 to penis 22 by fitting the male prosthesis and stimulator 10 over the glans of penis 22 and then unrolling the male prosthesis and stimulator 10 to enclose the shaft of penis 22. The glans of penis 22 is left uncovered so that it can be directly stimulated. Optionally, the user can apply a condom 26 over penis 22, engaging the O-ring 28 of condom 26 with ridge 20 to secure condom 26. During the sex act, the movement of filling 34 imparts pleasurable sensations to penis 22 and to the sexual partner. The enhanced girth of penis 22 resulting from the application of the male prosthesis and stimulator 10 may also impart pleasurable sensations to the sexual partner. Upon the conclusion of the sex act, the user removes condom 26 (if applicable), and then rolls up the male prosthesis and stimulator 10 along its circumference to remove it from the shaft of penis 22. The male prosthesis and stimulator 10 can be unrolled for washing. Once the male prosthesis and stimulator 10 has dried, it can be rolled up again along its circumference and replaced in container 30. Alternatively, the male prosthesis and stimulator 10 can simply be disposed of after use.

While a current embodiment of the male prosthesis and stimulator has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable material such as polyurethane, polypropylene film, polyethylene terephthalate film, ethylene/vinyl acetate copolymer films, ultra-high molecular weight polyethylene, polyester block amides, polyester elastomers, vinyl materials, or latexes may be used instead of the silicone ridge and tube described. Also, the bead and gel filling may also be made of, or include, saline solution. And although enhancing stimulation during intercourse has been described, it should be appreciated that the male prosthesis and stimulator herein described is also suitable for promoting erections by stabilizing the penis. Furthermore, a wide variety of shapes may be used instead of the arctuate and cylindrical shapes described.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A male prosthesis and stimulator comprising:

an outer wall having opposing ends and an outer surface; wherein said outer surface of said outer wall is adapted to receive the O-ring of a condom, wherein said adaptation comprises ridges attached to said outer surface of said outer wall;

an inner wall having opposing ends and an inner surface with said opposing ends attached to said opposing ends of said outer wall;

a hollow interior enclosed by said outer wall and said inner wall; and a filling contained by said interior.

* * * * *